United States Patent [19]

Maurice

[11] Patent Number: 4,842,401

[45] Date of Patent: Jun. 27, 1989

[54] EYE DIAGNOSIS PROCESS

[75] Inventor: David Maurice, Atherton, Calif.

[73] Assignee: The Board of Trustees of the Leland Stanford Jr. University, Palo Alto, Calif.

[21] Appl. No.: 62,213

[22] Filed: Jun. 15, 1987

[51] Int. Cl.⁴ .......................... A61B 3/10; A61B 5/00
[52] U.S. Cl. .................................. 351/221; 351/206; 128/633
[58] Field of Search .............. 351/205, 206, 221, 212, 351/247, 160 R; 128/633, 652, 654, 665

[56] References Cited

U.S. PATENT DOCUMENTS 4,412,543  11/1983  Vassiliadis et al. ............... 128/633
4,533,223  8/1985  Duparchy ........................ 351/206

Primary Examiner—Rodney B. Bovernick
Assistant Examiner—P. M. Dzierzynski
Attorney, Agent, or Firm—Flehr, Hohbach, Test, Albritton & Herbert

[57] ABSTRACT

An eye examination process includes instilling a neutral pH sulforhodamine B fluorescent dye which is excitable by green light and which fluoresces with orange light in the eye of a patient. The eye is then illuminated with green light and the eye is observed, preferably through a biomicroscope, through a filter which will pass orange light and which will not transmit the wavelength of the illuminating light. This process allows observation of both the eye's tear film and devitalized epithelial cells in the eye.

5 Claims, 2 Drawing Sheets

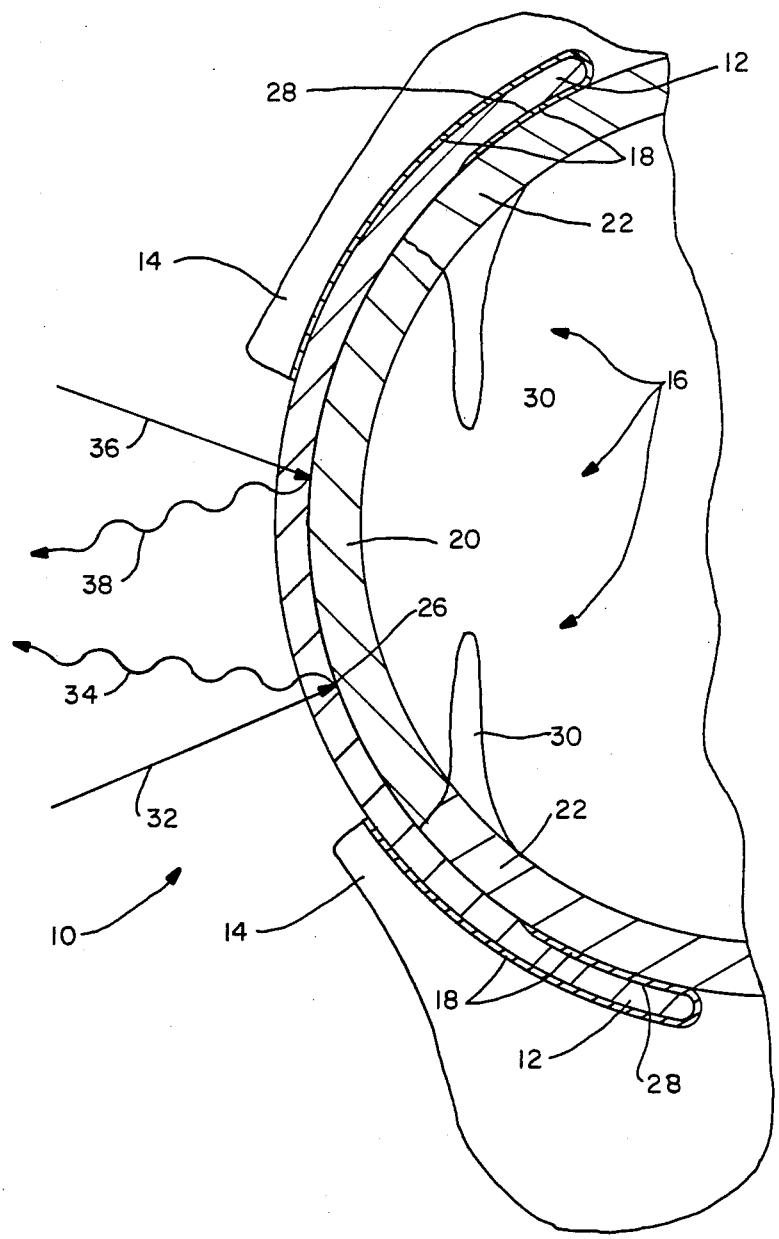
FIG.—1

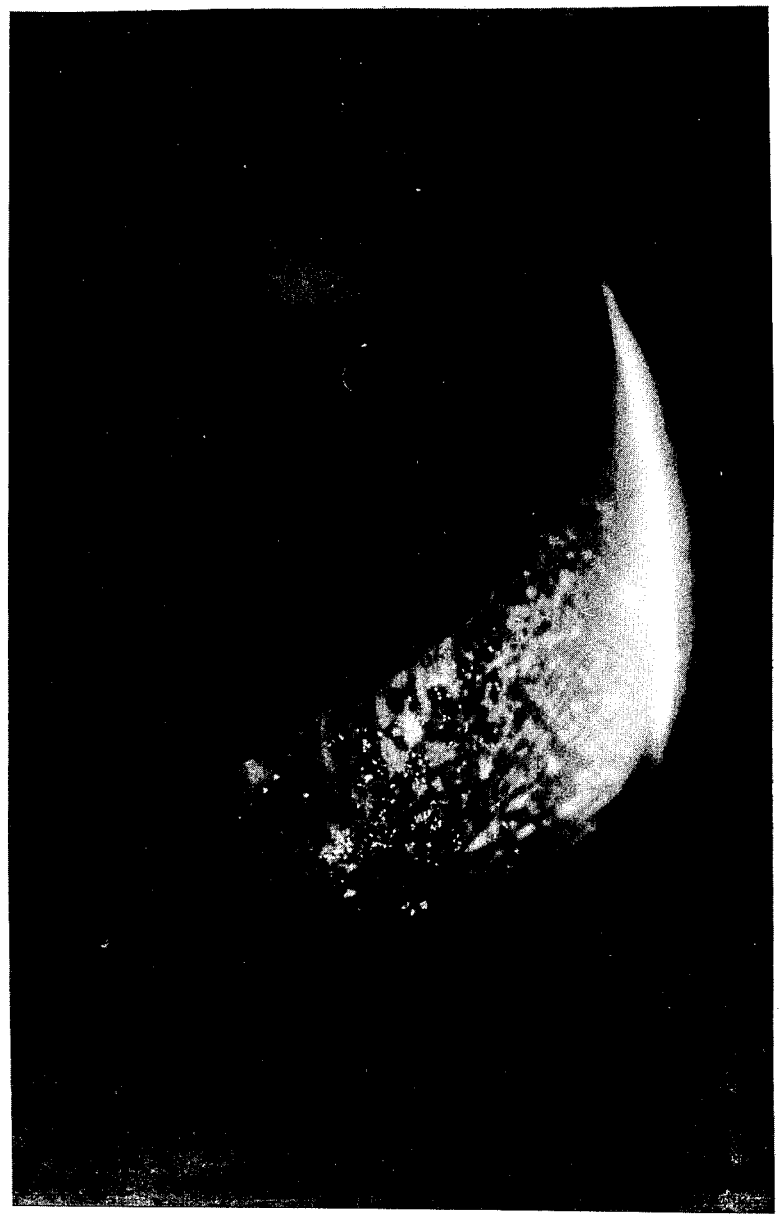
FIG.—2

EYE DIAGNOSIS PROCESS

This invention was developed under a government contract and may be manufactured or used by or for the government for governmental purposes without the payment of any royalty thereon or therefore.

BACKGROUND OF THE INVENTION

1. Field of the Invention

This invention relates to a process for observing structures of the eye for diagnostic purposes. More particularly, it relates to such a process for observing the tear film and of devitalized epithelial cells of the cornea and conjunctiva in order to aid in the diagnosis and to follow the progress of diseases of the surface of the eye and of the lacrimal system.

2. Description of the Prior Art

An aid to diagnosis of external diseases or superficial injuries of the eye is the introduction of small volumes of dye into the conjunctival cul-de-sac and examination of the eye with a biomicroscope. One dye commonly used for this purpose is fluorescein, whose green fluorescent color is observed by illumination with blue light. This allows the behavior of the tear film to be noted over the cornea, and it also reveals the presence of injuries to the superficial layer of epithelial cells of the cornea, which will be stained a bright green color by the dye. The use of fluorescein is of only limited value in making observations on the conjunctival membrane, because this membrane and its underlying sclera have a natural fluorescence when excited by blue light which conceals that of the dye itself. The fluorescein also penetrates the conjunctiva to some extent and makes the tear film and cells less visible in later stages.

Another dye commonly used is Rose Bengal, which colors injured cells pink and is used for observing devitalized cells in the conjunctival region, where they show up over the white background. However, Rose Bengal is painful when instilled into the eye and cannot be used in sufficient concentration to observe the tear film.

Because of these limitations in the known eye examination processes using dye to highlight the eye structures to be observed, a need remains for further improvement in such eye examination processes.

SUMMARY OF THE INVENTION

Accordingly, it is an object of this invention to provide an eye examination process which will allow the tear film and devitalized epithelial cells of the cornea and conjunctiva to be observed using the same dye solution.

It is another object of the invention to provide such an eye examination process using a dye that will fluoresce at a wavelength free of interference with the natural fluorescence of the eye.

The attainment of these and related objects may be achieved through use of the novel eye examination process herein disclosed. An eye examination process in accordance with this invention includes instilling a neutral pH fluorescent dye which is excitable by light having a wavelength of at least about 520 nanometers and which fluoresces at a wavelength greater than about 520 nanometers in the eye of a patient. The eye is then illuminated with light having a wavelength which will fluoresce the dye, and the eye is observed, preferably through a biomicroscope, through a filter which will pass light of the wavelength emitted by the dye and which will not transmit the wavelength of the illuminating light.

Under these circumstances, the tear film can be clearly observed over the conjunctival surface of the eye. After the tear film containing the fluorescent dye has been diluted by the natural flow of tears or washed out with dye free eyedrops, fluorescent devitalized cells which are stained by the fluorescent dye can be seen with great clarity, over both the conjunctival and corneal surfaces. The preferred fluorescent dye for practice of the process is sulforhodamine B.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 1 is a cross-section view of an eye, useful for understanding the process of this invention.

FIG. 2 is a photomicrograph of an eye, showing results obtained with the process of this invention.

DETAILED DESCRIPTION OF THE INVENTION

Turning now to the drawings, more particularly to FIG. 1, there is shown a human eye 10, depicting various parts that are mentioned in this description. Conjunctival cul-de-sacs 12 are located between eyelids 14 and eyeball 16, and are formed by the conjunctiva 18. The cornea 20 is centrally located at the front of the eyeball between the eyelids 14. The sclera 22 is located on the eyeball 16 around the cornea 20. Tear film 24 coats the front of the eyeball 16 and fills the conjunctival cul-de-sac 12. Epithelial cells 26 of the cornea 20 are located at the surface of the cornea beneath the tear film 24. Similarly, epithelial cells 28 are located on the surface of the conjunctiva 18 facing the conjunctival cul-de-sac 12. Iris 30 is located behind the cornea 20, inside the eyeball 16.

In the process of this invention, after the eye 10 has been instilled with the dye solution, light 32 having a wavelength of at least about 520 nm strikes the epithelial cells 26 of the cornea 20, which emit light 34 at a longer wavelength than the exciting light 32. Similarly, light 36 having a wavelength of at least about 520 nm strikes the tear film 24, which emits light 38 at a longer wavelength than the exciting light 36. With the eyelids 14 peeled back to expose the epithelial cells 28, a corresponding result would be obtained by shining light having a wavelength of at least about 520 nm on the cells 28. Examination of the tear film 24 and stained epithelial cells 26 and 28 is carried out visually through a biomicroscope, and photomicrographs, such as shown in FIG. 2, can be taken through the biomicroscope with either monochrome or color film. The sclera 22 and the conjunctiva 18 have a natural green fluorescence when excited by blue light, which conceals fluorescence of the cells when fluorescein is used as a dye solution, in accordance with the prior art.

In addition to the preferred sulforhodamine B dye, the process of this invention can employ other fluorescent dyes having similar or different characteristics as long as the wavelength of excitation of their fluorescence is longer than that which excites fluorescence in the conjunctiva 18 and sclera 22 of the eye 10. Such dyes should be nontoxic and painless and should be deeply colored and have a high efficiency of conversion of absorbed light to that emitted as fluorescence. For example, various other dyes in the rhodamine group as well as rhodamine conjugated dextrans may be used. The fluorescent dye is desirably employed as a neutral pH aqueous solution, containing from about 0.5 to about 5 weight percent of the fluorescent dye, preferably about 1 to about 2 weight percent of the dye.

To practice the process, a drop of the neutral aqueous solution of the dye is instilled in the eye of the patient. The tear film 24 may be observed immediately by illuminating the eye with green light, i.e., light of wavelengths in the band 520–560 nm, which causes the preferred rhodamine B dye to fluoresce with orange light, i.e., wavelengths in the band 570–650 nm. The conjunctiva 18 and sclera 22 do not fluoresce under illumination at this wavelength and provide a dark background against which the presence of the rhodamine B dye shows up with high contrast. Under these circumstances, the tear film 24 can be clearly observed over the conjunctiva 28 surface. The eye 10 is examined in a slit lamp through a biomicroscope with a green interference filter placed in the pathway of the illuminating light and with orange filters (e.g., Kodak No. 25) placed in the eyepieces of the biomicroscope. To observe stained cells 26 and 28, the dye is allowed to wash out from the tear film for several minutes as a result of the natural secretion of tears, or the process may be accelerated by washing out the conjunctival cul-de-sac 12 with an eyecup containing a saline solution, or by the repeated instillation of some commercially available tear substitute.

The following nonlimiting example represents a best mode contemplated by the inventor for practicing the process of the invention and explains the invention further.

One small drop of a 2% by weight neutral aqueous sulforhodamine B solution was instilled in a patient's eye. The eye was illuminated and examined according to the above procedure, and photographed through the biomicroscope three minutes after instillation of the solution to give the image of FIG. 2. The bright spots in the upper half of the generally crescent shaped image are stained cells in the conjunctiva. The streaks and patches below the bright spots are the tear film. The streaks and patches were brighter immediately after the instillation of the dye solution and faded as the dye washed out from the tear film. The bright spots remained for a substantial period of time because they are produced by stained, devitalized cells. The thin, bright band along the bottom of the image is the edge of the patient's lower eyelid. The dark region to the right of the crescent shaped image is the cornea. To a trained ophthalmologist, such images, especially when compared with corresponding images of healthy and diseased eyes or of the same eye during medical treatment, provide important information on the diagnosis and to follow the progress of diseases of the surface of the eye and of the lacrimal system.

Substitution of other fluorescent dye solutions efficiently excited by wavelengths longer than about 520 nm and which produce emitted light having a longer wavelength than the exciting light in the above procedure gives similar advantageous results.

It should now be readily apparent to those skilled in the art that a novel eye diagnosis process capable of achieving the stated objects of the invention has been provided. The process allows the tear film and stained epithelial cells to be observed with the same fluorescent dye solution. The tear film and stained epithelial cells fluoresce at wavelengths free of interference from the natural fluorescence of the eye.

It should further be apparent to those skilled in the art that various changes in form and detail of the invention as shown and described may be made. It is intended that such changes be included within the spirit and scope of the claims appended hereto.

What is claimed is:

1. A process for eye diagnosis, which comprises instilling into the eye a solution of a fluorescent dye which is excitable with a wavelength of light longer than a wavelength of light that will cause natural fluorescence in the eye B2, exciting the fluorescent dye in the eye with a wavelength of light longer than a wavelength that will cause natural fluorescence in the eye, and observing patterns of light produced by fluorescence of the dye in the eye, the fluorescent dye being responsive to exciting light having a wavelength of at least 520 nanometers and the exciting wavelength of light being at least 520 nanometers.

2. The process of claim 1 in which the patterns of light are produced by fluorescence of the dye in a tear film of the eye.

3. The process of claim 2 in which the patterns of light are produced by fluorescence of the dye in devitalized epithelial cells of the eye.

4. The process of claim 1 in which the patterns of light are observed through a color filter which will transmit light of a wavelength greater than the exciting light corresponding to the wavelength of the fluorescence, but which will block transmission of the exciting light.

5. The process of claim 1 in which the fluorescent dye comprises a solution of sulforhodamine B.

* * * * *